United States Patent [19]
Labruyere

[11] Patent Number: 5,844,126
[45] Date of Patent: Dec. 1, 1998

[54] METHOD AND DEVICE FOR DETERMINING THE SPEED OF PROPAGATION OF A TEMPERATURE WAVE FRONT IN A GAS

[75] Inventor: Yvan Labruyere, Montseveroux, France

[73] Assignee: Elf Antar France, Courbevoie, France

[21] Appl. No.: 731,490

[22] Filed: Oct. 16, 1996

[30] Foreign Application Priority Data

Oct. 19, 1995 [FR] France ................................ 95 12277

[51] Int. Cl.[6] ............................................. G01P 3/66
[52] U.S. Cl. ........................ 73/35.15; 73/116; 73/35.07
[58] Field of Search .............................. 73/35.07, 35.08, 73/35.15, 25.01, 115, 116

[56] References Cited

U.S. PATENT DOCUMENTS

| | | | |
|---|---|---|---|
| 4,203,726 | 5/1980 | Patterson | 73/25.01 |
| 4,308,519 | 12/1981 | Garcea et al. | 340/53 |

FOREIGN PATENT DOCUMENTS

| | | |
|---|---|---|
| 2 131 177 | 6/1984 | United Kingdom . |
| 2 175 703 | 12/1986 | United Kingdom . |
| WO 89/03520 | 4/1989 | WIPO . |

OTHER PUBLICATIONS

Review of Scientific Instruments, vol. 51, No. 11, pp. 1482–1484, Nov. 1980, D. Sengupta, et al., "Direct Display of Electron Temperature Oscillation in a Plasma".

International Laboratory, vol. 14, No. 7, pp. 50–56, Sep. 1984, T. Dokter, et al., "Microprocessor–Based Technique for Measuring Flame Speeds and Other Fast Phenomena".

*Primary Examiner*—John E. Chapman
*Attorney, Agent, or Firm*—Oblon, Spivak, McClelland, Maier & Neustadt, P.C.

[57] ABSTRACT

The propagation of a temperature wave front in an enclosed space containing a gas features the measurement of the time which elapses between the passage of a temperature wave front past two thermionic probes 5, 6 mounted on the wall 4 of an enclosed space 3 arranged substantially along an axis 9 of propagation of the wave front and separated by a known distance.

3 Claims, 3 Drawing Sheets

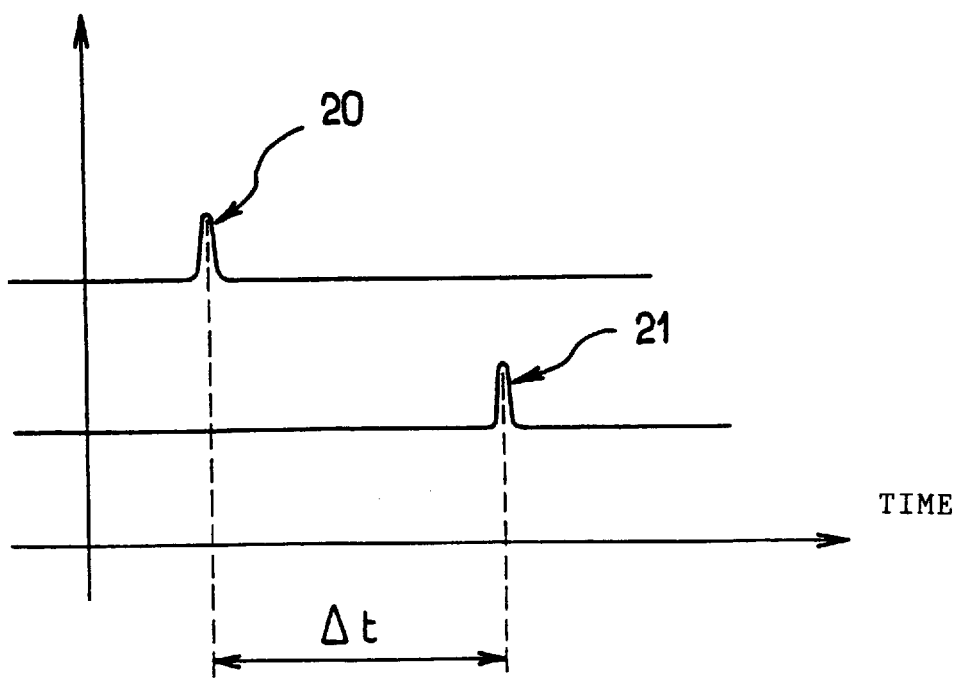
FIG_3

METHOD AND DEVICE FOR DETERMINING THE SPEED OF PROPAGATION OF A TEMPERATURE WAVE FRONT IN A GAS

BACKGROUND OF THE INVENTION

1. Field of the Invention

Investigating combustion in motor vehicle engines requires knowledge of one of the important intrinsic properties of a fuel mixture, namely the laminar speed of propagation of the flame.

This speed depends on the composition of the mixture, on its temperature and on its pressure.

2. Discussion of Background

A device for measuring this speed is described in the document "LA COMBUSTION DANS LES MOTEURS D'AUTOMOBILE [COMBUSTION IN MOTOR VEHICLE ENGINES]", from the colloquium of the engines scientific group, Rueil Malmaison (France) of 5 Nov. 1987, published by "Editions Technip" Paris.

This device includes an experimental engine derived from a production engine and designed to give optical access to the combustion chamber, especially through a quartz window, a laser beam generator, optical means for processing this beam and a high-speed camera.

This device makes it possible to watch the progression of the flame through the combustion chamber and by interpreting the images recorded, allows the speed of propagation of the flame to be determined.

This device is very expensive, and it is also difficult and time-consuming to use. It does not allow the speed of propagation of the flame in the combustion chamber of an engine to be measured without substantially modifying this engine, nor does it allow the evolution of this speed as a function, for example, of the parameters of engine setting or of the fuel, to be monitored.

This device is also limited by the recording speed of the high-speed camera. In practical terms it is limited to observing phenomena on engines running at speeds of less than 5000 rpm.

A known method for determining the speed of a flame front is the method known as the spherical chamber method. This method makes it possible to achieve, from a central ignition point, a constant-volume combustion and a flame front which is assumed to remain smooth, spherical and symmetric with respect to the center of the chamber, over time.

The speed of the flame front is calculated from measuring the dynamic pressure in the enclosed space and by means of a dynamic combustion model which relies on the characteristic parameters of the combustible mixture.

This method cannot be applied to the measurement of the speed of propagation of a flame front in a variable-volume enclosed space, such as the combustion chamber of a combustion engine or a gas turbine.

It is therefore poorly suited to the investigation of fuels and of engines.

SUMMARY OF THE INVENTION

The precise objective of the present invention is to overcome these drawbacks and in particular to provide a method and a device for determining the speed of propagation of a temperature wave front in a gas contained in an enclosed space, especially a variable-volume enclosed space.

This method and this device can be used in centers for investigating engines, gas turbines and compressors. They allow these items of equipment to be investigated as a function of the setting and operating parameters, as well as allowing the combustibles and fuels with which they are fed to be investigated.

This method and this device are easy to use, they require no substantial modifications to the enclosed spaces in which the speed of propagation of the temperature front is being measured nor do they require the use of complex mathematical models for calculating the speed from the quantities measured.

To this end, the invention proposes a method for determining the speed of propagation of a temperature wave front in a gas contained in an enclosed space, characterized in that the time which elapses between the passage of the wave front past two electric-charge-detection probes which have response times of below 10 microseconds, mounted on a wall of the said enclosed space, arranged substantially along an axis of propagation of the said wave front and separated by a known distance is measured.

According to another feature of the invention, the electric-charge-detection probes are thermionic probes.

Another subject of the invention is a device for determining the speed of propagation of a temperature wave front in a gas characterized in that it includes, on the one hand, an enclosed space containing the said gas and equipped with means for producing a temperature wave front and, on the other hand, at least two electric-charge-detection probes which have response times of below ten microseconds, fixed to a wall of the said enclosed space, arranged substantially along an axis of propagation of the wave front, separated by a known distance, the said probes being connected to electronic time-measurement means which separates the signals which they emit in turn at the moments the temperature wave front passes each of them.

According to another feature of the device of the invention, the electric-charge-detection probes are thermionic probes.

Finally, according to a specific embodiment of the device of the invention, the enclosed space is a combustion chamber of a combustion engine comprising at least one cylinder inside which there travels a piston, closed at one of its ends by a cylinder head on which at least one spark plug is mounted, the temperature wave front being created by the combustion of a combustible mixture injected into the combustion chamber and ignited by the spark plug, the electric-charge-detection probes being mounted on the said cylinder head.

BRIEF DESCRIPTION OF THE DRAWINGS

The invention will be better understood with the aid of the attached drawings in which:

FIG. 3 represents a time graph of the signals emitted by the electric-charge-detection probes.

DETAILED DESCRIPTION OF THE INVENTION

In general, the method and the device of the invention are used to determine the speed of propagation of a temperature wave front in a hot gas contained in an enclosed space.

They are suitable for enclosed spaces of constant or variable volume.

Figure 1:
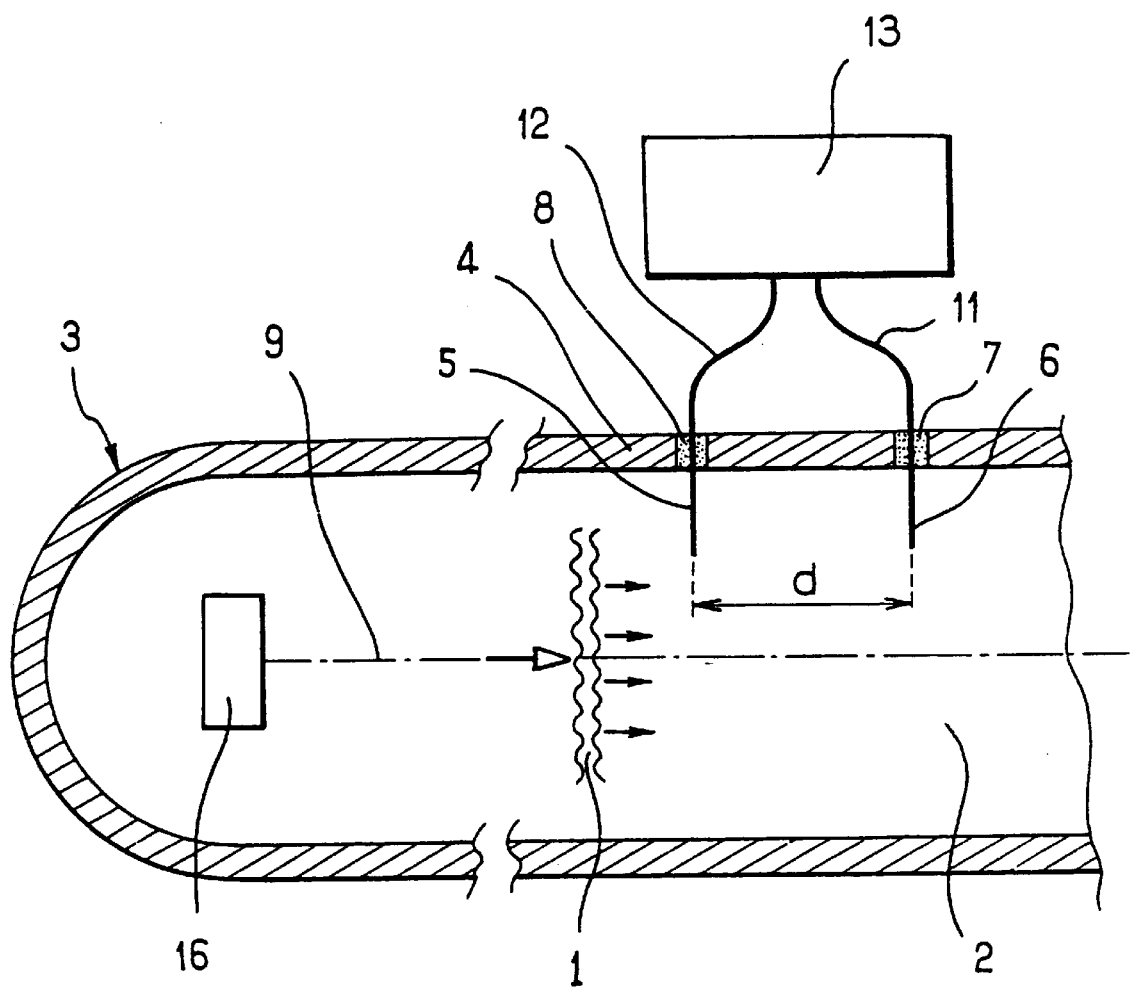
FIG. 1 diagrammatically represents the constituent parts of the device of the invention

FIG. 1 represents one embodiment of the device of the invention which includes:

an enclosed space 3 which delimits an area 2 containing a gas means 16 for producing at least one temperature wave front 1 two probes 5 and 6 for detecting electric charge which are mounted on the wall 4 of the enclosed space 3 insulated passages 7 and 8 passing through the wall 4 electronic measurement means 13 means 11 and 12 for electrically connecting the probes 5 and 6 to the electronic measurement means 13.

The device also includes, although these are not represented, means for introducing a gaseous combustible mixture into the enclosed space 3 and means for exhausting the burnt gases from the said enclosed space.

The electric-charge-detection probes 5 and 6 are arranged along an axis 9 of propagation of the temperature wave front 1, some distance d apart.

The probes 5 and 6 are electrically connected to the electronic measurement means 13 by the electrical connection means 11 and 12.

The temperature wave fronts, which are generated by the means 16 of producing wave fronts in the gas 2, propagate along the axis 9.

A temperature wave front is characterized by the presence of three electrical charges in the hot gas which locally modify the value of the electric field.

When a wave front passes the probes 5 and 6, electric currents are induced in each one of them.

The signals emitted by these passages of a temperature wave front through the probes 5 and 6 have the form of pulses like those represented in FIG. 3.

The time $\Delta t$ separating the pulses emitted respectively by the probes 5 and 6 is measured by the electronic means 13.

The speed of propagation of the temperature wave front is, by definition, given by the relationship:

$$v = d/\Delta t$$

in which v represents the speed of propagation along the axis 9 of the temperature wave front in cm/s d represents the distance separating the probes in cm $\Delta t$ represents the time separating the signals emitted by the probes upon passage of the wave front in seconds.

This speed can be calculated automatically by the electronic measurement means 13 using appropriate software.

According to a preferred embodiment, the electric-charge-detection probes 5 and 6 are thermionic probes.

These probes work on the phenomenon of thermionic emission of metals. A given metal is characterized by the energy W, known as the work function which corresponds to the energy that has to be supplied to an electron in the conduction band of this metal for this electron to leave the metal.

By way of example, here are the values of W for the following metals:

caesium: W=1.8 eV
potassium: W=2.2 eV
molybdenum: W=4.4 eV
gold: W=4.9 eV
nickel: W=5.05 eV (1 eV is equivalent to $0.16 \cdot 10^{-18}$ joules)

The thermal excitation energy of each electron in the conduction band of a metal increases with its temperature. This energy may become greater than W for some of them which may leave the metal, travelling at a certain speed.

If, near the emissive metal, there is a prevailing electric field which opposes the leaving of the electrons if this field is strong enough, it will repel the electrons towards the metal.

If on the other hand the field is an accelerating field, it will be easier for the electrons to leave the metal, and an electric current will flow in the metal.

This is what is observed when a temperature wave front passes close to a thermionic probe.

FIG. 3 represents the pulses 20 and 21 of electric current emitted one after the other by each of the probes 5 and 6 as a function of time, as the temperature front passes each of them.

Figure 2A:
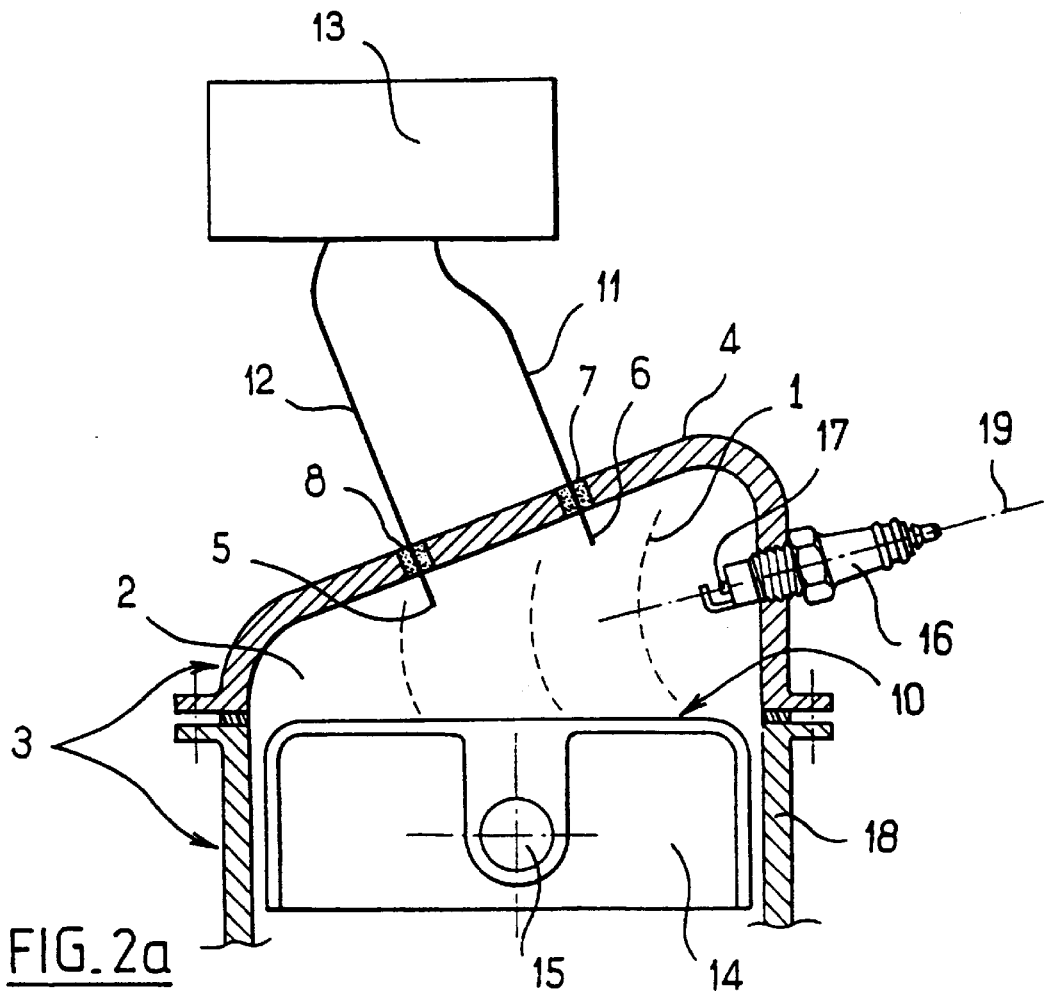
FIGS. 2a and 2b show the parts of a device for measuring the speed of propagation of a temperature wave front in a cylinder head of a combustion engine, in longitudinal section and in cross section respectively
Figure 2B:
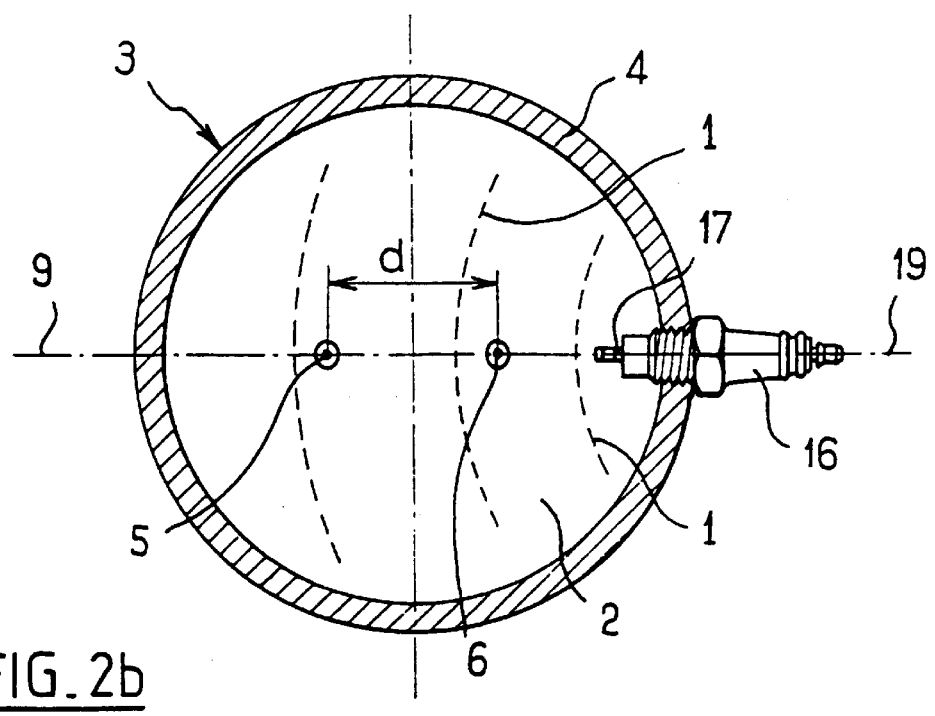

According to a specific embodiment of the invention, represented diagrammatically by FIGS. 2a and 2b, the device of the invention is applied to the determination of the speed of propagation of the temperature wave front travelling in the combustion chamber 2 of a combustion engine which includes:

a cylinder 18 with a diameter substantially equal to 54 mm a piston 14 a cylinder head 4 a spark plug 16 with its insulated electrode 17 two electric-charge-detection probes 5 and 6 mounted on the cylinder head 4 insulated passages 7 and 8 passing through the cylinder head 4 electronic measurement means 13 means 11 and 12 for electrically connecting the probes 5 and 6 to the electronic measurement means 13.

The combustion engine includes other parts necessary for its operation, but not represented, especially means for injecting the air/fuel mixture into the chamber 2 and exhaust valves for the burnt gases.

The combustion chamber 2 is delimited by the top face 10 of the piston 14, the internal face of the cylinder 18, and the internal face of the cylinder head 4.

The volume of the combustion chamber 2 varies as a function of the position of the piston 14 in the cylinder 18.

The probes 5 and 6 are mounted substantially in the plane normal to the axis 15 of the piston passing through the axis 19 of the spark plug 16. The electrode 17 of the spark plug 16 is also in the same plane.

The probes 5 and 6 will advantageously be thermionic probes, in the form of needles with a diameter of between 0.3 and 2 mm, and preferably a diameter of 0.5 mm, of which that part which projects into the combustion chamber 2 is between 1 and 2 mm long. The distance between the probes 5 and 6 is, for example, 25 mm.

Other forms of probe will easily be produced by those skilled in the art, for example cylinders with a diameter of 4 mm, of which the part which projects into the combustion chamber 2 is substantially 0.5 mm long.

These probes, because of their small dimensions, can easily be mounted on most engines, and cause practically no disruption to the operation thereof.

In order to investigate the propagation of the temperature wave front in a plane parallel to the top face 10 of the piston, several probes, 6 for example, are mounted at the periphery of the cylinder head.

I claim:

1. Method for determining the speed of propagation of a temperature wave front in a gas contained in an enclosed space, characterized in that the time which elapses between the passage of the wave front past two thermionic probes which have response times of below 10 microseconds, mounted on a wall of the said enclosed space, arranged substantially along an axis of propagation of the said wave front and separated by a known distance (d) is measured.

2. Device for determining the speed of propagation of a temperature wave front in a gas characterized in that it includes, on the one hand, an enclosed space containing the said gas and equipped with means for producing a temperature wave front and, on the other hand, at least two thermionic probes and which have response times of below ten microseconds, fixed to a wall of the said enclosed space, arranged substantially along an axis of propagation of the wave front, separated by a known distance (d), the said probes and being connected to electronic time-measurement means which separates the signals which they emit in turn at the moments the temperature wave front passes each of them.

3. Device according to claim 2, characterized in that the enclosed space is a combustion chamber of a combustion engine comprising at least one cylinder inside which there travels a piston, closed at one of its ends by a cylinder head on which at least one spark plug is mounted, the temperature wave front being created by the combustion of a combustible mixture injected into the combustion chamber and ignited by the spark plug, the electric-charge-detection probes being mounted on the said cylinder head.

* * * * *